United States Patent
Kumar et al.

(10) Patent No.: US 11,624,116 B2
(45) Date of Patent: Apr. 11, 2023

(54) BIOASSISTED TREATMENT OF MICROBIOLOGICALLY INFLUENCED CORROSION IN PETROLEUM TRANSPORTING PIPELINES

(71) Applicant: Indian Oil Corporation Limited, Mumbai (IN)

(72) Inventors: Manoj Kumar, Haryana (IN); Prakash Chandra Sahoo, Haryana (IN); Suresh Kumar Puri, Haryana (IN); Sankara Sri Venkata Ramakumar, Haryana (IN)

(73) Assignee: Indian Oil Corporation Limited, Mumbai (IN)

( * ) Notice: Subject to any disclaimer, the term of this patent is extended or adjusted under 35 U.S.C. 154(b) by 98 days.

(21) Appl. No.: 17/232,311

(22) Filed: Apr. 16, 2021

(65) Prior Publication Data

US 2021/0324526 A1     Oct. 21, 2021

(30) Foreign Application Priority Data

Apr. 17, 2020  (IN) .............................. 202021016688

(51) Int. Cl.
| | | |
|---|---|---|
| *C23F 15/00* | (2006.01) | |
| *C09K 8/54* | (2006.01) | |
| *C12Q 1/24* | (2006.01) | |
| *C12N 11/02* | (2006.01) | |
| *B82Y 5/00* | (2011.01) | |
| *B82Y 40/00* | (2011.01) | |

(52) U.S. Cl.
CPC ................ *C23F 15/00* (2013.01); *C09K 8/54* (2013.01); *C12N 11/02* (2013.01); *C12Q 1/24* (2013.01); *B82Y 5/00* (2013.01); *B82Y 40/00* (2013.01); *C09K 2208/32* (2013.01)

(58) Field of Classification Search
None
See application file for complete search history.

(56) References Cited

U.S. PATENT DOCUMENTS

| | | |
|---|---|---|
| 8,585,899 B2 | 11/2013 | Baldwin et al. |
| 9,453,247 B2 | 9/2016 | Summer et al. |
| 9,464,267 B2 | 10/2016 | Summer et al. |
| 9,650,272 B2 | 5/2017 | Summer et al. |
| 9,732,369 B2 | 8/2017 | Pilloni et al. |
| 10,085,445 B2 | 10/2018 | Fuji et al. |
| 2013/0116126 A1* | 5/2013 | Ashby .................... C12P 5/023 435/252.4 |
| 2014/0030306 A1 | 1/2014 | Polizzotti et al. |
| 2016/0215920 A1 | 7/2016 | Mogensen et al. |
| 2016/0360749 A1 | 12/2016 | He et al. |
| 2019/0023975 A1 | 1/2019 | Shim et al. |

FOREIGN PATENT DOCUMENTS

| | | |
|---|---|---|
| WO | WO-2009/076642 A2 | 6/2009 |
| WO | WO-2019/014061 A1 | 1/2019 |

* cited by examiner

*Primary Examiner* — Jeffrey D Washville
(74) *Attorney, Agent, or Firm* — Blank Rome LLP

(57) ABSTRACT

The present invention relates to a method for reducing or preventing the formation or activity of a corrosion-associated biofilm on a metal surface, wherein the method comprises contacting the metal surface with a liquid composition comprising biocidal preparation. The present invention also relates to a microbicidal composition comprising at least one alcohol, one liquid hydrocarbon, a bacteriophage immobilized on a magnetic nanocomposite, at least one phage releasing reagent and one stabilizer. The microbicide composition and method of the present invention reduces biofilms on surfaces, and consequently, reduces, mitigates, or eliminates MIC in internal surface of the oil transporting pipelines.

10 Claims, No Drawings

BIOASSISTED TREATMENT OF MICROBIOLOGICALLY INFLUENCED CORROSION IN PETROLEUM TRANSPORTING PIPELINES

RELATED APPLICATION

This application claims the benefit of Indian Application No. 202021016688, filed on Apr. 17, 2020. The entire disclosure of this application is hereby incorporated by reference.

FIELD OF THE INVENTION

The present invention relates to a method for reducing or preventing the formation or activity of a corrosion-associated biofilm on a metal surface. The present invention also relates to a microbicidal composition comprising at least one alcohol, one liquid hydrocarbon, a bacteriophage immobilized on a magnetic nanocomposite, at least one phage releasing reagent and one stabilizer.

BACKGROUND OF THE INVENTION

Microbiologically influenced corrosion (MIC) is defined as damage to engineered materials and processing systems that is mediated by living organisms. Oil and gas production, distribution and refining systems are particularly vulnerable for microbiologically influenced corrosion (MIC) activities and can lead to corrosion in metallic assets and associated losses.

The main classes of microbes associated with biofouling are sulfate-reducing bacteria (SRB), iron-oxidizing/reducing bacteria (IRB), microbes secreting organic acids (APB), exopolymers or slime producing microbes (SPB), methanogen, nitrate reducing bacteria, low nutrient bacteria etc. These organisms, in most of the cases, coexist in naturally occurring biofilms, often forming synergistic communities that can affect electrochemical processes through co-operative metabolism generally not seen in the individual. Corrosion caused by microbes result in pitting on metal surface and results in extensive damage to oil and gas storage, production, and transportation equipment. Pipe systems, tank bottoms, and other pieces of oil production equipment can rapidly fail if there are areas where microbial corrosion is occurring. If a failure occurs in a pipeline or oil storage tank bottom, the released oil can have serious environmental consequences.

A variety of strategies have been described to mitigate MIC, including, the use of corrosion-resistant metals, temperature control, pH control, radiation, filtration, protective coatings with corrosion inhibitors or other Chemical controls i.e., biocides, bacteriological controls i.e., phages, competitive microflora, pigging (i.e., mechanical removal of muck and corrosion products), anodic and cathodic protection, and modulation of nutrient levels etc. However, these methods are generally high cost, lack of effectiveness, short lifespan, or requirement of repeated application.

Combination of pigging and biocide dosing is the most used approach for controlling MIC in oil and gas transporting pipelines. Pigging removes the muck and biofilm on the pipe surfaces, but several time biocide treatments is less effective due to their poor permeability and requires frequent dosing or some time continuous dosing. Commonly, biocides are dosed at high concentration which is environmentally reactive. The solubility of biocide to oil phase is also an issue. Thus, there is an urgent need for a method and composition that not only overcome the drawbacks associated with the existing compositions and methods but also provides an effective solution for reducing and/or mitigating the MIC in the pipelines.

WO 2019/014061 discloses compositions and methods for controlling souring and corrosion causing prokaryotes, such as SRP, by treating oil and gas field environments or treatment fluids with a newly identified bacterial strain PTA-124262 as a self-propagating whole cell that produces an anti-SRP bacteriocin in-situ. In another aspect, the methods use one or more toxic peptides or proteins isolated therefrom in methods to control unwanted prokaryotic growth in these environments.

US 2019/0023975 relates to biocide compositions, formulations, and methods for using formulations. U.S. Pat. No. 9,732,369 provides a multi-phase process for conditionally treating MIC by evaluating whether MIC-correlating conditions exist, the degree of MIC, if present, and then applying a concomitant MIC-mitigating treatment which is adjusted in its degree of aggressiveness in proportion to MIC severity. The disclosed methodology allows, in part, for the continuous or periodic monitoring and assessment of MIC risk in petroleum-based equipment (e.g., pipeline) and the administering of a treatment that corresponds to the level of severity of the MIC resulting in a more fine-tuned, localized, and cost-effective treatment.

U.S. Pat. No. 10,085,445 provide an agent for inhibiting biocorrosion of a metal, which shows high environmental and occupational safety.

US 20160360749 describes methods for mitigating or eliminating MIC of a metal surface including contacting the metal surface with an effective amount of a liquid composition comprising indole or a functionally equivalent analog or derivative thereof. Also provided are methods for reducing the formation or activity of a corrosion-associated biofilm on a metal surface including contacting the metal surface with an effective amount of a liquid composition including indole or a functionally equivalent analog or derivative thereof.

U.S. Pat. No. 9,464,267 describes a process for remediation of target bacteria, particularly sulfur reducing bacteria (SRB), in waters having a multiplicity and diverse host target bacteria by employing serial or staged bacteria culturing and lysing of dominant bacteria. Remediation of Sulfur reducing bacteria (SRB) is effected by application of a series of bacteriophage isolated from the staged culturing and bacteriophage lysing of successive aliquots of waters containing a multiplicity of SRB.

U.S. Pat. No. 9,650,272 describes a safe, natural, environmentally sound means of controlling bacterial contamination, corrosion, and souring of oil and gas wells and reservoirs that result from bacteria-contaminated water in a well.

U.S. Pat. No. 9,453,247 relates to a method of reducing process interruptions in biofuel production systems by reducing the amount of unwanted bacteria in the biofuel production system by the use of an effective amount of one or more types of bacteriophages virulent for at least some strains of the unwanted bacteria.

WO 2009076642 describes a method of reducing biocorrosion or biofilm blockage in by identifying a target suspected of comprising one or more bio-corrosive organisms and delivering to the target suspected of comprising the bio-corrosive organisms an effective amount of a composition comprising an infective virulent viral panel sufficient to reduce the amount of bio-corrosive organisms at the target.

U.S. Pat. Nos. 9,453,247 and 8,585,899 disclose the development of a cocktail of phage selective for one type of bacterial group. However, present invention overcomes this feature and provides a composition and method to inhibit all groups of microbes.

US 2014030306A1, US 2016215920A1 discloses biocidal and antimicrobial properties of bacteriophage. Cellulose Chem. Technol., 47 (9-10), 727-734 (2013) teaches the highly absorbent nature of $Fe_3O_4$ magnetic nano particles (MNPs) towards lignin. However, none of the existing art has disclosed the immobilization of phage on lignin and magnetite/hematite.

WO 2009076642A2 describes aqueous medium as delivery medium for phage. However, present invention uses the hydrocarbon medium as delivery in medium and can be delivered in the pipeline in presence of fluid including diesel, hexadecane, alcohols, gasoline, ATF, Naphtha etc.

WO 2009076642A2 and U.S. Pat. No. 9,453,247 describes the nonspecific release of phage. However, present invention discloses the targeted release of phage at MIC site.

U.S. Pat. No. 9,650,272B2 describes a method of controlling bacterial contamination, corrosion, and souring of oil and gas wells and reservoirs that result from bacteria-contaminated water in a well. In one aspect, it is a process for remediation of souring of petroleum reservoirs and coalbeds by adding to the water used in flooding and "fracing" operations an effective number of virulent bacteriophages specific for problematic target bacteria.

It can be seen that the existing solutions for addressing the MIC in pipelines require higher biocide concentration for all group of causative agents/dosing are required, which is environmental reactive/hazardous. Further, continuous dosing of biocide and follow-up is required, which is expensive. Microbes also develop resistance to biocides. Mixture of crude and biocide are discarded during MIC mitigation process in pipeline. Since, this invention does not require any chemicals, it is environmentally benign. In case of phage-based treatment, phages are used against one specific group of MIC causing microbes, which does not result in complete reduction of MIC problem in any pipeline segment. The phage cocktail developed in this invention is effective against all group of MIC causing microbes present in any pipeline.

The primary object of the present invention is to provide a method for mitigating or eliminating microbially influenced corrosion (MIC) at a site of interest i.e., a metal surface of an equipment for refining, storing, transporting of oil and natural gas.

Another object of the present invention is to provide a microbicide composition for mitigating or eliminating biofilms on metal surfaces, and consequently, reducing, mitigating, or eliminating MIC in internal surface of the oil transporting pipelines.

Yet another object of the present invention is to develop a cocktail of bacteriophage effective to all groups of MIC inducing microorganisms present in any pipeline segment.

Still another object of the present invention is to develop immobilized or encapsulated bacteriophages useful in a method for mitigating or eliminating the formation or activity of a corrosion-associated biofilm on a metal surface of the oil transporting pipelines.

SUMMARY OF THE INVENTION

The present disclosure relates to a method for mitigating or eliminating microbially influenced corrosion (MIC) at a site of interest i.e., a metal surface of an equipment for refining, storing, transporting of oil and natural gas is provided. The present disclosure also relates to a microbicide composition comprising at least one alcohol, one liquid hydrocarbon, bacteriophage immobilized on a magnetic nanocomposite, at least one phage releasing reagent and one stabilizer for mitigating or eliminating microbiologically influenced corrosion (MIC) at a site of interest.

In an embodiment, the present disclosure provides a method for mitigating or eliminating microbially influenced corrosion (MIC) at a site of interest, said method comprising:

(i) obtaining sample from the site of interest and identifying and culturing target bacterial strain by known methods;

(ii) identifying and obtaining bacteriophage against MIC causing microbes from the above sample;

(iii) immobilizing or encapsulating the obtained bacteriophages on a nano-magnetic particle, nano-lignin and a combination thereof;

(iv) preparing microbicide corrosion inhibitor composition by adding at least one phage releasing agent and a stabilizer to a combined solution of alcohol and hydrocarbon followed by adding immobilized or encapsulated phages;

(v) subjecting the site of interest with the microbicide composition to effect a reduction or elimination of microbially influenced corrosion (MIC) wherein the culturing of bacterial strain in step (i) is performed in the presence of microbial antibiotics in a sub-optimal concentration of $\frac{1}{15}^{th}$ of minimum inhibitory concentration and wherein the bacteriophages are selectively released at a pH in the range of 6.5 to 4 in MIC condition.

In an embodiment, the present disclosure provides a method for mitigating or eliminating microbially influenced corrosion (MIC) at a site of interest, wherein the bacteriophages are immobilized on magnetic nanoparticle using binders having terminal aldehyde or epoxy groups and wherein the binders are selected from the group comprising glutaraldehyde, and diglycidyl ether.

In an embodiment, the present disclosure provides a method for mitigating or eliminating microbially influenced corrosion (MIC) at a site of interest, wherein the immobilization of bacteriophages is attained by any of the process selected among ultrasonication, shaking, covalent or charge directed immobilization process.

In an embodiment, the present disclosure provides a method for mitigating or eliminating microbially influenced corrosion (MIC) at a site of interest, wherein the nano-magnetic particle or nano lignin is functionalized with amine or carboxylic functionalizing agent and is having a carbon chain of length between 3 to 12; and wherein the functionalizing agent is having exposed primary or secondary amine, amino acids, amine functionalized metal organic frameworks or chitosan or N-hydroxysuccinimide, 1-ethyl-3-(3-(dimethylamino)propyl) carbodiimide hydrochloride.

In an embodiment, the present disclosure provides a method fix mitigating or eliminating microbially influenced corrosion (MIC) at a site of interest, wherein the alcohol in microbicide composition in step (iv) of process as described herein is selected from the group consisting of ethanol, isopropanol, glycol, ethylene glycol, diethylene glycol, 1, 2-propylene glycol, dipropylene glycol, tripropylene glycol, glycol ether, butyl glycol, butyl diglycol, a glycol ester, butyl diglycol acetate, 2, 2, 4-trimethylpentanediol monoisobutyrate, polyethylene glycol, polypropylene glycol, benzyl alcohol, n-butyl alcohol, benzyl alcohol, 2,4-dichlorobenzyl alcohol and 2-phenoxyethanol and a combination thereof.

In an embodiment, the present disclosure provides a method for mitigating or eliminating microbially influenced corrosion (MIC) at a site of interest, wherein the hydrocarbon in microbicide composition in step (iv) of process as described herein is selected from the group consisting of diesel, petrol, kerosene, alkenes, cyclohexane and a petroleum refining liquid fuel.

In an embodiment, the present disclosure provides a method for mitigating or eliminating microbially influenced corrosion (MIC) at a site of interest, wherein the phage releasing reagent in microbicide composition in step (iv) of process as described herein is a protic and aprotic ionic liquid and is selected from the group consisting of 1-Benzyl-3-methylimidazolium tetrafluoroborate ([BzMIM] [BF4]), 1-Butyl-3-methylimidazolium chloride ([BMIM] [Cl]), Triethylammonium acetate (TEAA), Choline dihydrogen phosphate ([Chol] [DHP]), Choline serinate ([Chol] [Ser]), Ethylammonium nitrate (EAN), Tetrabutylphosphonium bromide (TBPBr) and a combination thereof.

In an embodiment, the present disclosure provides a method for mitigating or eliminating microbially influenced corrosion (MIC) at a site of interest, wherein the stabilizer in microbicide composition in step (iv) of process as described herein is selected from the group consisting of N,N-dimethylethanolamines, such as (N,N-dimethylaminoethoxy) ethanol; dimethylethanolamine; triethanolamine; methyl diethanol amine; ethanolamine; diethanolamine; other cyclic amines including morpholine, methyl morpholine, ethylmorpholine, piperidine, alkylpiperidines, piperazine, alkyl piperazines; ethylene amines including DETA, TETA, TEPA, and the like; alkyl amines including methyl amine, dimethyl amine, alkyl methylamines, dimethyl alkylamines; methyl amino propylamine; dimethyl aminopropylamine; dimethyl aminoethylamine; methyl aminoethylamine and a combination thereof.

In an embodiment, the present disclosure provides a method for mitigating or eliminating microbially influenced corrosion (MIC) at a site of interest, wherein the site of interest is a metal surface of an equipment for refining, storing, transporting of oil and natural gas.

In an embodiment, the present disclosure provides a method for mitigating or eliminating microbially influenced corrosion (MIC) at a site of interest, wherein the step (v) of process comprising subjecting the site with microbicide composition as described herein is preceded by repetitive chain of pigging with the help of cleaning brush pig.

In an embodiment, the present disclosure provides a method for mitigating or eliminating microbially influenced corrosion (MIC) at a site of interest, wherein target bacterial strain is an anaerobic bacterium causing corrosion by depositing bacterial biofilm on the metal surface.

In an embodiment, the present disclosure provides a method for mitigating or eliminating microbially influenced corrosion (MIC) at a site of interest, wherein the target bacterial strain is selected from the group consisting of sulfate-reducing bacteria (SRB), iron-oxidizing/reducing bacteria (IRB), bacteria secreting organic acids (APB), exopolymers or slime (SPB), methanogen, nitrate reducing bacteria and low nutrient bacteria and a combination thereof.

In an embodiment, the present disclosure provides a method for mitigating or eliminating microbially influenced corrosion (MIC) at a site of interest, wherein the sample is a muck sample obtained from Municipal solid waste (MSW), Sewage treatment plant (STP) or any industrial wastewater samples by pigging.

In an embodiment, the present disclosure provides a method for mitigating or eliminating microbially influenced corrosion (MIC) at a site of interest, wherein the microbicide composition comprising bacteriophages in an amount of at least $10^9$ PFU mL$^{-1}$; at least one alcohol in amount of 50-75% (vol/vol); a hydrocarbon in an amount of 25-50% (vol/vol); at least one phage releasing agent in an amount of 1-5 ppm; and a stabilizer in an amount of 6-10 ppm is effective for reducing or eliminating microbially influenced corrosion (MIC) at the site of interest.

In another aspect, the present disclosure relates to a microbicide composition for mitigating or eliminating microbiologically influenced corrosion (MIC) at a site of interest, said composition comprising:

(i) bacteriophages in an amount of at least $10^9$ PFU mL$^{-1}$;
(ii) at least one alcohol in amount of 50-75% (vol/vol);
(iii) a hydrocarbon in an amount of 25-50% (vol/vol);
(iv) at least one phage releasing agent in an amount of 1-5 ppm; and
(v) a stabilizer in an amount of 6-10 ppm.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps of the process, features of the product, referred to or indicated in this specification, individually or collectively, and any and all combinations of any or more of such steps or features.

Definitions

For convenience, before further description of the present disclosure; certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally equivalent products and methods are clearly within the scope of the disclosure, as described herein.

In accordance with the present invention, a method for mitigating or eliminating microbially influenced corrosion (MIC) at a site of interest i.e., a metal surface of an equipment for refining, storing, transporting of oil and natural gas is provided. The present disclosure also provides a microbicide composition comprising at least one alcohol, one liquid hydrocarbon, bacteriophage immobilized on a magnetic nanocomposite, at least one phage releasing reagent and one stabilizer for mitigating or eliminating microbiologically influenced corrosion (MIC) at a site of interest.

In an embodiment, the present disclosure provides a method for mitigating or eliminating microbially influenced corrosion (MIC) at a site of interest, said method comprising:
(i) obtaining sample from the site of interest and identifying and culturing target bacterial strain by known methods;
(ii) identifying and obtaining bacteriophage against MIC causing microbes from the above sample;
(iii) immobilizing or encapsulating the obtained bacteriophages on a nano-magnetic particle, nano-lignin and a combination thereof;
(iv) preparing microbicide corrosion inhibitor composition by adding at least one phage releasing agent and a stabilizer to a combined solution of alcohol and hydrocarbon followed by adding immobilized or encapsulated phages;
(v) subjecting the site of interest with the microbicide composition to effect a reduction or elimination of microbially influenced corrosion (MIC) wherein the culturing of bacterial strain in step (i) is performed in the presence of microbial antibiotics in a sub-optimal concentration of $\frac{1}{15}^{th}$ of minimum inhibitory concentration and wherein the bacteriophages are selectively released at a pH in the range of 6.5 to 4 in MIC condition.

In an embodiment, the present disclosure provides a method for mitigating or eliminating microbially influenced corrosion (MIC) at a site of interest, wherein the bacteriophages are immobilized on magnetic nanoparticle using binders having terminal aldehyde or epoxy groups and wherein the binders are selected from the group comprising glutaraldehyde, and diglycidyl ether.

In an embodiment, the present disclosure provides a method for mitigating or eliminating microbially influenced corrosion (MIC) at a site of interest, wherein the immobilization of bacteriophages is attained by any of the process selected among ultrasonication, shaking, covalent or charge directed immobilization process.

In an embodiment, the present disclosure provides a method fix mitigating or eliminating microbially influenced corrosion (MIC) at a site of interest, wherein the nano-magnetic particle or nano lignin is functionalized with amine or carboxylic functionalizing agent and is having a carbon chain of length between 3 to 12; and wherein the functionalizing agent is having exposed primary or secondary amine, amino acids, amine functionalized metal organic frameworks or chitosan or N-hydroxysuccinimide, 1-ethyl-3-(3-(dimethylamino)propyl) carbodiimide hydrochloride.

In an embodiment, the present disclosure provides a method for mitigating or eliminating microbially influenced corrosion (MIC) at a site of interest, wherein the microbicide composition comprising bacteriophages in an amount of at least $10^9$ PFU $mL^{-1}$; at least one alcohol in amount of 50-75% (vol/vol); a hydrocarbon in an amount of 25-50% (vol/vol); at least one phage releasing agent in an amount of 1-5 ppm; and a stabilizer in an amount of 6-10 ppm is effective for reducing or eliminating microbially influenced corrosion (MIC) at the site of interest.

In an embodiment, the present disclosure provides a method for mitigating or eliminating microbially influenced corrosion (MIC) at a site of interest, wherein the alcohol in microbicide composition in step (iv) of process is selected from the group consisting of ethanol, isopropanol, glycol, ethylene glycol, diethylene glycol, 1, 2-propylene glycol, dipropylene glycol, tripropylene glycol, glycol ether, butyl glycol, butyl diglycol, a glycol ester, butyl diglycol acetate, 2, 2, 4-trimethylpentanediol monoisobutyrate, polyethylene glycol, polypropylene glycol, benzyl alcohol, n-butyl alcohol, benzyl alcohol, 2,4-dichlorobenzyl alcohol and 2-phenoxyethanol and a combination thereof.

In an embodiment, the present disclosure provides a method for mitigating or eliminating microbially influenced corrosion (MIC) at a site of interest, wherein the hydrocarbon in microbicide composition in step (iv) is selected from the group consisting of diesel, petrol, kerosene, alkenes, cyclohexane and a petroleum refining liquid fuel.

In an embodiment, the present disclosure provides a method for mitigating or eliminating microbially influenced corrosion (MIC) at a site of interest, wherein the phage releasing reagent in microbicide composition in step (iv) f process is a protic and aprotic ionic liquid and is selected from the group consisting of 1-Benzyl-3-methylimidazolium tetrafluoroborate ([BzMIM] [BP4]), 1-Butyl-3-methylimidazolium chloride ([BMIM] [Cl]), Triethylammonium acetate (TEAA), Choline dihydrogen phosphate ([Chol] [DHP]); Choline serinate ([Chol] [Ser]), Ethylammonium nitrate (EAN), Tetrabutylphosphonium bromide (TBPBr) and a combination thereof.

In an embodiment, the present disclosure provides a method for mitigating or eliminating microbially influenced corrosion (MIC) at a site of interest, wherein the stabilizer in microbicide composition in step (iv) of process is selected from the group consisting of N,N-dimethylethanolamines, such as (N,N-dimethylaminoethoxy) ethanol; dimethylethanolamine; triethanolamine; methyl diethanol amine; ethanolamine; diethanolamine; other cyclic amines including morpholine, methyl morpholine, ethylmorpholine, piperidine, alkylpiperidines, piperazine, alkylpiperazines; ethylene amines including DETA, TETA, TEPA, and the like; alkyl amines including methyl amine, dimethyl amine, alkyl methylamines, dimethyl alkylamines; methyl amino propylamine; dimethyl aminopropylamine; dimethyl aminoethylamine; methyl aminoethylamine and a combination thereof.

In an embodiment, the present disclosure provides a method for mitigating or eliminating microbially influenced corrosion (MIC) at a site of interest, wherein the site of interest is a metal surface of an equipment for refining, storing, transporting of oil and natural gas.

In an embodiment, the present disclosure provides a method for mitigating or eliminating microbially influenced corrosion (MIC) at a site of interest, wherein the step (v) of subjecting the site with microbicide composition is preceded by repetitive chain of pigging with the help of cleaning brush pig.

In an embodiment, the present disclosure provides a method for mitigating or eliminating microbially influenced corrosion (MIC) at a site of interest, wherein the sample is a muck sample obtained from Municipal solid waste (MSW), Sewage treatment plant (STP) or any industrial wastewater samples by pigging.

In an embodiment, the present disclosure provides a method for mitigating or eliminating microbially influenced corrosion (MIC) at a site of interest, wherein target bacterial strain is an anaerobic bacterium causing corrosion by depositing bacterial biofilm on the metal surface.

In an embodiment, the present disclosure provides a method for mitigating or eliminating microbially influenced corrosion (MIC) at a site of interest, wherein the target bacterial strain is selected from the group consisting of sulfate-reducing bacteria (SRB), iron-oxidizing/reducing bacteria (IRB), bacteria secreting organic acids (APB), exopolymers or slime (SPB), methanogen, nitrate reducing bacteria and low nutrient bacteria and a combination thereof.

Bacteriophage or phage is a virus that infects and replicates within bacteria and archaea.

In accordance with the present invention, the method of isolation of bacteriophage cocktail effective for all microbes comprises of:
1. Collecting muck samples from pipeline to be treated for MIC or from MSW, STP or any industrial wastewater samples. In case of microbes isolated from muck samples obtained from MSW, their activity was tested against MIC causing microbes;
2. Incubating said muck sample in appropriate media in an environment conducive for growth of microbes;
3. Adding microbial antibiotics in a sub-optimal concentration i.e., $\frac{1}{15}^{th}$ of minimum inhibitory concentration;
4. Adding 10 ml of water from STP/any industrial wastewater like refinery ETP/ or 10-gram soil from oil contaminated soil to the muck sample in media at step 3;
5. Incubating the sample of step 4 for 96 hours under same condition;
6. Adding 10 ml the STP water again to sample of step (5) and incubating it for 48 hours;
7. Allowing the bacterial culture obtained at step 6 to grow under anaerobic and aerobic condition from the muck sample for 24-120 hours and the bacterial count to be observed;
8. Once zero bacterial count is observed, the supernatant was collected and tested for the presence of bacteriophage against MIC causing microbes;
9. Repeat once steps 3-7 using the supernatant test and after completion of step-7 and adding fresh muck sample from the subject pipeline;
10. The isolated phage can be immobilized on material including but not limited to lignin and magnetic particle.

In accordance with the present invention, the phage media may include 6% MSW, STP or any industrial waste water in modified SM media having following composition (g/L): Mannitol 1.5-2.5, isopropanol 10.0-12.0, L-Glutamic acid 1.0-2.0, Magnesium sulfate, $7H_2O$ 0.16-0.19, Manganese sulfate, $H_2O$ 0.31-0.35 mg, Potassium phosphate, monobasic 0.02-0.3 mg, Zinc sulfate, $7H_2O$ 0.55-0.70 mg, Ferric ammonium sulfate, $6H_2O$ 0.09 mg-1.0 mg, Copper sulfate, $5H_2O$ 0.01-0.3 mg, Calcium sulfate, $5H_2O$ 0.01-0.5 mg, Phosphoric acid 0.005-0.007 mg, Potassium iodide 0.000006 mg-0.000010, Final pH (at 25° C.) 6.0-6.5.

In accordance the present invention, the antibiotics which can be used in suboptimal conditions includes Penicillins, Tetracyclines, Cephalosporins, Quinolones, Lincomycins, Macrolides, Sulfonamides, Glycopeptides, Aminoglycosides, Carbapenems.

In accordance the present invention, the antibiotics more specifically includes penicillin, amoxicillin, doxycycline, cephalexin, ciprofloxacin, clindamycin, metronidazole, azithromycin.

In accordance with the present invention, the bacteriophages described herein is tolerant to alcohol up to 100% and is having the ability to tolerance in 100% petrol, kerosene or any other alkenes like cyclohexane or a mixture of them.

In accordance with the present invention, the bacteriophages described herein have the ability to etch extracellular polymeric substances (EPS) developed during microbial bio-film formation and make the cell structure of MIC causing microbes not to develop resistance towards phages.

The phage described in the present invention is highly specific to MIC microbes found in petroleum pipelines. So, selection of bacteriophage is specific to the pipeline. No specific phage can be developed to mitigate MIC in various pipelines.

In an embodiment of the present invention, the phage described herein must be imbibed in host medium by immobilization or encapsulation.

In yet another embodiment, the bacteriophages were immobilized on magnetic nanoparticle using binders having terminal aldehyde or epoxy groups. The binders may include but not limited to glutaraldehyde or diglycidyl ether.

In one embodiment, the magnetic colloidal nanoparticles may contain a core shell having any magnetic material in the core. The core may contain magnetic metal oxide crystals, magnetic fluid or magnetic quantum dot or magnetic composites. In accordance with the present invention, the magnetic materials may include but are not limited to Fe—Co, Fe—Ni, Fe—Pt, Co—Pt, Co—Ni, $Fe_3O_4$, $\gamma Fe_2O_3$, $NiFe_2O_4$, $MnFe_2O_4$, $CoFe_2O_4$, NiO, $Co_3O$, $Fe_3O_4$ hollow spheres.

In an embodiment, the outside of the nano-magnetic particle may be coated with any natural or synthetic polymer. In yet another embodiment, the size of core shell magnetic nano particle before coating should be between 1-50 nm. The nanoparticle described herein must be stabilized in alcohol, petrol, kerosene or any other alkenes like cyclohexane.

In yet another embodiment, the magnetic nanoparticle may be functionalized with amine or carboxylic functionalization. The carbon chain of the functionalizing agent should be between 3 to 12. The functionalized material may include but limited to any polymer coating having exposed primary or secondary amine, amino acids, amine functionalized metal organic frameworks or chitosan or N-hydroxysuccinimide, 1-ethyl-3-(3-(dimethylamino)propyl) carbodiimide hydrochloride.

In accordance with the invention, lignin can be obtained from any plant material including but not limited to rice husk, clover, corn cobs, wheat straw, jute, oat straw, barley straw, jute stick, *eucalyptus*, bagasse, *eucalyptus*, spruce wood, bamboo, peanut shells, spruce wood, and coconut shells. The same can be functionalized by alkylation of the hydroxyl group by reaction with amine. The amine function of lignin can be active by its reaction with at least one of alkyl amine, alkyl amine sulfates, alkylene amine such as methyl amine, N-{3-chloro-2-hydroxypropyl) trimethylammonium chloride, polymer coating having exposed primary or secondary amine, amino acids, amine functionalized metal organic frameworks or chitosan or N-hydroxysuccinimide, 1-ethyl-3-(3-(dimethylamino) propyl) carbodiimide hydrochloride or combinations thereof.

The amine functionalizing agent for magnetic nanoparticle and nano lignin may further include but are not limited to straight-chained and branched-chained primary and secondary polyamines such as polyalkyleneamines and polyalkylene polyamines, e.g., ethylenediamine, diethylenetriamine, triethylenetetramine, tetraethylenepentamine, pentaethylenehexamine, and others, such as, for example, 1, 2- or 1, 3-propanediamine, 1,4-butanediamine, 1,5-pentanediamine, 1,3,5-pentanediamine, and the like. The polyalkylenamines such as ethylenediamine, diethylenetriamine, triethylenetetramine, and tetraethylenepentamine constitute the polyamines of choice in the practice of this invention. Homologues (both linear and branched-chained) of the aforementioned polyalkyleneamines may also be used, if desired. These homologues differ from their respective polyamine by one or more units of CH2-CH2-N and are usually coproduced during the manufacture of the polyalkyleneamines.

In an embodiment of the present invention, the binding of bacteriophages may be carried by ultrasonication or shaking. In another embodiment, the bacteriophages can be immobilized on nano-magnetic particle and nano lignin by covalent or charge directed immobilization process. In yet another embodiment, the combination of magnetic nano particle and nano lignin can be used for bacteriophage immobilization.

In an embodiment of the invention, the final biocide cocktail or microbicidal composition was prepared by mixing immobilized bacteriophage where the concentration of bacteriophages is above $10^9$ PFU mL$^{-1}$, 50-75% alcohol, 25-50% hydrocarbons like diesel, petrol, kerosene or any other alkenes like cyclohexane or petroleum refining liquid fuel, 1-5 ppm phage releasing reagent and 6-10 ppm stabilizer.

In another embodiment, the alcohols include but are not limited to ethanol and isopropanol, a glycol, e.g., ethylene glycol, diethylene glycol, 1, 2-propylene glycol, dipropylene glycol, and tripropylene glycol, a glycol ether, e.g., butyl glycol and butyl diglycol, a glycol ester, e.g., butyl diglycol acetate or 2, 2, 4-trimethylpentanediol monoisobutyrate, a polyethylene glycol, a polypropylene glycol, benzyl alcohol, n-butyl alcohol, benzyl alcohol, 2,4-dichlorobenzyl alcohol, 2-phenoxyethanol and combinations thereof.

In yet another embodiment, the phage releasing reagent may include both protic and aprotic ionic liquids. It may include but are not limited to 1-Benzyl-3-methylimidazolium tetrafluoroborate ([BzMIM] [BF4]), 1-Butyl-3-methylimidazolium chloride ([BMIM] [Cl]), Triethylammonium acetate (TEAA), Choline dihydrogen phosphate ([Chol] [DHP]), Choline serinate ([Chol] [Ser]), Ethylammonium nitrate (EAN), Tetrabutylphosphonium bromide (TBPBr) or a combination thereof.

The stabilizer may include but not limited to N,N-dimethylethanolamines, such as (N,N-dimethylaminoethoxy) ethanol; dimethylethanolamine; triethanolamine; methyl diethanol amine; ethanolamine; diethanolamine; other cyclic amines including morpholine, methyl morpholine, ethylmorpholine, piperidine, alkylpiperidines, piperazine, alkylpiperazines; ethylene amines including DETA, TETA, TEPA, and the like; alkyl amines including methyl amine, dimethyl amine, alkyl methylamines, dimethyl alkylamines; methyl amino propylamine; dimethyl aminopropylamine; dimethyl aminoethylamine; methyl aminoethylamine and combinations thereof.

Present invention further discloses a method to reduce, mitigate, or eliminate MIC in internal surface of the oil transporting pipelines. In one aspect, the disclosure relates to a method for mitigating or eliminating Microbial Influenced Corrosion of a metal surface comprising contacting the metal surface with the microbicide composition as described in accordance with the present invention.

The subject pipelines are first cleaned using repetitive chain of pigging with the help of cleaning brush pia. Once the pipeline is clean; the microbicidal dosing is initiated. Before starting microbicidal dosing a plug is created using Bi-di pig and first batch of microbicide is dosed through the launching barrel of the pipeline. Subsequent batches of microbicide are dosed in similar way and the biocide plug is closed by launching another pig after the last dose of biocide. Once microbicide dosing is completed a chain of pig run for attest two times is done to remove the debris, if any. The treatment result is reduced or no microbial count in the muck sample subsequent cleaning pig run.

In an embodiment, the pipeline is first treated with pigging. Pigging helps to physically remove the biofilm, and also acts to disturb the biofilm such that the permeation of the biofilm is improved, thereby rendering the microbicidal treatment more effective. The major steps of the making the biocide plug in the pipeline is as follows:

1. Launching of 1st Bi-Di pig (with transmitter) after venting & draining of launching barrel;
2. Crude oil injection through kicker line to push the pig into the main pipeline, BV (Barrel Valve) & KLV (Kicker Line Valve) kept fully opened and closure of MLV (Main Line Valve);
3. Venting & draining of launching barrel to be done such that any traces of vapors & oil gets outside barrel and pressure inside barrel becomes zero;
4. After proper closing of barrel door, injection of second dose of microbicides into the barrel again as much possible and opening of KLV & BV with MLV in still close condition;
5. Running of booster pumps and crude oil injection to push Biocide batch into mainline for 10 min approximately;
6. The step 2-5 can be repeated several times or repeat can be avoided;
7. 2nd Bi-Di pig (with transmitter) is inserted after venting & draining of launching barrel;
8. Once Pig starts moving, the same to be tracked with the help of Pig Alert/Tracker and operation through MLPLUs to be resumed;
9. MLV to be opened followed by closure of KLV & BV.

The minimum inhibiting concentration and killing dose and time for the microbicidal composition is decided as per standard method known in prior art. In another embodiment the selective release of phage was started from pH 6.5 to 4 in MIC condition.

In another aspect, the present disclosure provides a microbicide composition for mitigating or eliminating microbiologically influenced corrosion (MIC) at a site of interest, said composition comprising:
(i) bacteriophages present in an amount of at least $10^9$ PFU ML$^{-1}$;
(ii) at least one alcohol present in the range of 50-75% (vol/vol);
(iii) one hydrocarbon present in the range of 25-50% (vol/vol);
(iv) at least one phage releasing agent present in the range of 1-5 ppm; and
(v) one stabilizer present in the range of 6-10 ppm.

In an embodiment, the present disclosure provides a microbicide composition for mitigating or eliminating microbiologically influenced corrosion (WC) at a site of interest, said composition comprising:
(i) bacteriophages present in an amount of at least $10^9$ PFU mL$^{-1}$;
(ii) at least one alcohol present in the range of 50-75% (vol/vol);

(iii) one hydrocarbon present in the range of 25-50% (vol/vol);
(iv) at least one phage releasing agent present in the range of 1-5 ppm; and
(v) one stabilizer present in the range of 6-10 ppm.
wherein the bacteriophages are immobilized or encapsulated on a nano-magnetic particle.

In an embodiment, the present disclosure provides a microbicide composition for mitigating or eliminating microbiologically influenced corrosion (MIC) at a site of interest, said composition comprising:
(i) bacteriophages present in an amount of at least $10^9$ PFU mL$^{-1}$;
(ii) at least one alcohol present in the range of 50-75% (vol/vol);
(iii) one hydrocarbon present in the range of 25-50% (vol/vol);
(iv) at least one phage releasing agent present in the range of 1-5 ppm; and
(v) one stabilizer present in the range of 6-10 ppm.
wherein the bacteriophages are immobilized or encapsulated on a nano-lignin particle.

In an embodiment, the present disclosure provides a microbicide composition for mitigating or eliminating microbiologically influenced corrosion (MIC) at a site of interest, said composition comprising:
(i) bacteriophages present in an amount of at least $10^9$ PFU mL$^{-1}$;
(ii) at least one alcohol present in the range of 50-75% (vol/vol);
(iii) one hydrocarbon present in the range of 25-50% (vol/vol);
(iv) at least one phage releasing agent present in the range of 1-5 ppm; and
(v) one stabilizer present in the range of 6-10 ppm.
wherein the bacteriophages are immobilized or encapsulated on a nano-magnetic particle, nano-lignin and a combination thereof.

In an embodiment, the present disclosure provides a microbicide composition for mitigating or eliminating microbiologically influenced corrosion (MIC) at a site of interest, wherein the alcohol is selected from the group consisting of ethanol, isopropanol, glycol, ethylene glycol, diethylene glycol, 1, 2-propylene glycol, dipropylene glycol, tripropylene glycol, glycol ether, butyl glycol, butyl diglycol, a glycol ester, butyl diglycol acetate, 2, 2, 4-trimethyl-pentanediol monoisobutyrate, polyethylene glycol, polypropylene glycol, benzyl alcohol, n-butyl alcohol, benzyl alcohol, 2,4-dichlorobenzyl alcohol, 2-phenoxyethanol and a combinations thereof.

In an embodiment, the present disclosure provides a microbicide composition for mitigating or eliminating microbiologically influenced corrosion (MIC) at a site of interest, wherein the hydrocarbon is selected from the group consisting of diesel, petrol, kerosene, alkenes, cyclohexane and a petroleum refining liquid fuel.

In an embodiment, the present disclosure provides a microbicide composition for mitigating or eliminating microbiologically influenced corrosion (MIC) at a site of interest, wherein the phage releasing reagent is a protic and aprotic ionic liquid.

In an embodiment, the present disclosure provides a microbicide composition for mitigating or eliminating microbiologically influenced corrosion (MIC) at a site of interest, wherein the phage releasing reagent is selected from the group consisting of 1-Benzyl-3-methylimidazolium tetrafluoroborate ([BzMIM] [BF4]), 1-Butyl-3-methylimidazolium chloride ([BMIM] [Cl]), Triethylammonium acetate (TEAA), Choline dihydrogen phosphate ([Chol] [DHP]), Choline serinate ([Chol] [Ser]), Ethylammonium nitrate (EAN), Tetrabutylphosphonium bromide (TBPBr) and a combination thereof.

In an embodiment, the present disclosure provides a microbicide composition for mitigating or eliminating microbiologically influenced corrosion (MIC) at a site of interest, wherein the stabilizer is selected from the group consisting of N,N-dimethylethanolamines, such as (N,N-dimethylaminoethoxy) ethanol; dimethylethanolamine; triethanolamine; methyl diethanol amine; ethanolamine; diethanolamine; other cyclic amines including morpholine, methyl morpholine, ethylmorpholine, piperidine, alkyl piperidines, piperazine, alkylpiperazines; ethylene amines including DETA, TETA, TEPA, and the like; alkyl amines including methyl amine, dimethyl amine, alkyl methylamines, dimethyl alkylamines; methyl amino propylamine; dimethyl aminopropylamine; dimethyl aminoethylamine; methyl aminoethylamine and a combination thereof.

In an embodiment, the present disclosure provides a microbicide composition for mitigating or eliminating microbiologically influenced corrosion (MIC) at a site of interest, wherein the bacteriophages are selectively released at a pH in the range of 6.5 to 4 in MIC condition.

In an embodiment, the present disclosure provides a microbicide composition for mitigating or eliminating microbiologically influenced corrosion (MIC) at a site of interest, wherein the bacteriophages are immobilized or encapsulated on a nano-magnetic particle, nano-lignin and a combination thereof.

In an embodiment, the present disclosure provides a microbicide composition for mitigating or eliminating microbiologically influenced corrosion (MIC) at a site of interest, wherein the nano-magnetic particle or nano lignin is functionalized with amine or carboxylic functionalizing agent.

In an embodiment, the present disclosure provides a microbicide composition for mitigating or eliminating microbiologically influenced corrosion (MIC) at a site of interest, wherein the site of interest is a metal surface of an equipment for refining, storing, transporting of oil and natural gas.

Although the subject matter has been described in considerable detail with reference to certain preferred embodiments thereof, other embodiments are possible.

Having described the basic aspects of the present invention, the following non-limiting examples illustrate specific embodiment thereof.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods, the exemplary methods, devices and materials are described herein. It is to be understood that this disclosure is not limited to particular methods, and experimental conditions described, as such methods and conditions may vary.

Example-1—Isolation of Bacteriophage

The present invention is with premise of isolating/enriching the phage which are effective against all the microbes present in any pipeline segment. The source of phage will be either hydrocarbon contaminated soil, sewage treatment plant (STP) water, STP sludge, refinery effluent treatment plant (ETP) aeration tank water or any such source in which normally phages are found. The phage source will be incubated with muck sample and phages will be allowed to grow on the bacteria present in the muck sample by providing such optimum conditions. The phage present in muck sample will also propagate. Such enriched phage solution will be separated according to the knowledge disclosed in prior art and will be used to its ability to kill the microbes present in the muck sample of subject pipelines. For the same, muck sample will be exposed to enriched phages and microbial count with and without phage treatment will be monitored. If the phage treated has reduced microbial count, the phage solution will be immobilized and suspended as the present invention and will be used for treatment of that subject pipelines. If the microbial count is not reduced >20% of the muck sample without phage treatment, the enrichment will be done for two to six more cycle with the same muck and phage source. After 2-6 cycles the phage concentration is always such that it can reduce the microbial count to >20% of the muck sample.

For the isolation of bacteriophages and MIC causing microbes, 100 gram of muck samples was aseptically collected from Balasore Station of Paradip-Haldia-Barauni Oil Pipeline (PHBPL) of Indian Oil Corporation Ltd., during pigging operation. The pipeline originates at Paradip Port, Jagatsinghpur district, Odisha, and terminates at the IOCL Barauni Refinery, Bihar.

10 gram of muck sample collected was introduced aseptically in each of the 100 ml media i.e., Postgate E media for SRB, media for APB, Iron-related bacteria (IRB), aerobic heterotrophic bacteria Slime forming bacteria (SFB).

The Postgate E media consisting of (g/l) $KH_2PO_4$-0.5; $NH_4Cl$-1; $Na_2SO_4$-0.1; $CaCl_2.6H_2O$-1; $MgCl_2.7H_2O$-2, Sodium lactate-3.5; Yeast extract-1; Ascorbic acid-0.2; Thioglycolic acid-0.2 and Ferrous sulphate-0.5 g. The APBs media consist of (g/l) $KH_2PO_4$-0.2; $(NH_4)_2SO_4$-2.0; $MgSO_4$-0.24; $KCl_2$-0.10; Yeast extract-0.10; Glucose-2.0 and Phenol red as indicator. The Iron-related bacteria (IRB) consist of (g/l) $FeSO_4.7H_2O$-1.0; Ammonium sulfate-0.15; Potassium chloride 0.05; $MgSO_4.7H_2O$-0.5; $KH_2PO_4$-0.05 and Calcium nitrate-0.01. The aerobic heterotrophic bacteria (HAB) consist of yeast extract 10; peptone 10; sodium chloride 05; Dibasic potassium phosphate 2.5 and Glucose 2.5. Slime forming bacteria (SFB) media containing (g/l) Yeast extract 0.1; Peptone-0.5; $MgCl_2$-0.2 and NaCl-1.6. The SRB media was incubated anaerobically for 96 hours while other media were incubated in shaking conditions at 200 rpm for 48 hours. All media with muck sample were incubated at 30° C.

After said incubation time, all content were mixed in a container under nitrogen atmosphere and kept under microaerophilic conditions (MixBac-A).

The 10-gram soil from hydrocarbon contaminated site was aseptically collected in a collection tank and to this 100 ml of SM media was added.

SM media (composed of (g/L): Mannitol 1.5, isopropanol 10.0, L-Glutamic acid 1.0, Magnesium sulfate, $7H_2O$ 0.16, Manganese sulfate, $H_2O$ 0.31 mg, Potassium phosphate monobasic 0.02 mg, Zinc sulfate, $7H_2O$ 0.55 mg, Ferric ammonium sulfate, $6H_2O$ 0.09 mg, Copper sulfate, $5H_2O$ 0.01 mg, Calcium sulfate, $5H_2O$ 0.01 mg, Phosphoric acid 0.005 mg, Potassium iodide 0.000006 mg, Final pH (at 25° C.) 6.0-6.5). The obtained sample were spun gently in a homogenizer for 2 hours continuously and then centrifuged at 3000 rpm for 20 min. The supernatant was collected and recentrifuged at 5000 rpm for 20 min in refrigerated centrifuge. Then, supernatant was filtered through a 0.45 μm millipore syringe filters. The resultant filtrate was introduced in the container having muck sample with different media under microaerophilic conditions (MixBac-A) and incubated at 200 rpm at 30 degree C. for 96 hrs. After 96 hrs the supernatant was collected and introduced to fresh MixBac-A and this was repeated for 3 more times. Subsequently, the mixture was used for phage isolation.

Phage were isolated from above mixture using a standard phage enrichment method as described in the prior art. Chloroform was added to 0.1% of the sample volume and bacterial cell debris removed by a combination of centrifugation and filtration through a 0.22 mm pore size filter. Agar overlays were prepared by mixing 10 gram of muck sample with top 0.7 g/L agar and 10 μl drops of the phage enrichment were spotted. Clearings were observed following seven-day incubation at 37° C. The concentration of phage in the sample was determined by method know in prior through serially diluted phage stock into the muck top agar/bacterial host suspension agar plates.

Example 2: Immobilization of Bacteriophages on Modified Magnetic Particles

A. Synthesis of Functionalized Nanoparticle 10 mmoles of ferric chloride and 1 gram of PVA were mixed in 100 ml of ethanol/water (1:1) solution. 10 mmol of ferrous chloride was dissolved in 5 ml of water and added dropwise to the solution. The solution was stirred with drop-wise addition of 4.5 ml of 30% ammonium hydroxide and stirred at 70° C. for 1 hour. The resulting particles were separated by a magnet. The colloid had a size of ~60-100 nm by light scattering.

To 10 ml of nano particle (10 mg/ml), 0.1 M Tetramethylethylenediamine (TEMED) buffer (pH 5) and 0.2 g of 1-ethyl-3-(dimethylaminopropyl) carbodiimide hydrochloride at room temperature was added followed by 0.5 ml 1,2 ethylene diamine was added. The solution after stirring was centrifuged and washed three times in deionised water.

B. Immobilization of Bacteriophages on Modified Magnetic Particles

Immobilization of bacteriophages on modified magnetic particles were performed by overnight incubation of 1 ml of $10^9$ pfu/ml viruses with 5 ml of modified magnetic beads (10 mg/ml), with gentle shaking at room temperature on an orbital rotator for 3 h. The unbound bacteriophages were removed by washing the magnetic particles six times with phosphate buffered saline and Tween 20 solution (0.5 mM) (PBST).

Bacteriophages linked to magnetic particles were collected using a permanent magnet, re-suspended in 1 ml of 0.5 mM PBST buffer, and stored at 4° C. until they were used.

Bacteriophages were enumerated in the initial solution, supernatant/washing solutions, and the number of phages immobilized on magnetic particles was estimated by subtraction.

Example 3—Immobilization of Bacteriophages on Modified Lignin Nanoparticle

A. Synthesis of Lignin Nano Particle

Lignin nanoparticle was prepared by hydrochloric acidolysis followed by stabilization. A solution of 5 wt. % of lignin in ethylene glycol was prepared and stirred for 2 hours at 45° C., then hydrochloric acid (0.2 M) and $HNO_3$ (0.2 M) were separately added to lignin solutions at a rate of 5 drop/min until reaching the set pH values of 2.

0.02M Sodium bis-(2-ethylhexyl)-sulfosuccinate was added to the solution dropwise as stabilizer. The reaction was retained for another 2 hours after and then filtered to remove the insoluble impurities from lignin.

The solution was then dialyzed against deionized water for 24 hours and a final pH of 7.0 was obtained.

To functionalize the lignin nano particle 0.02 mM triethylene tetramine and stirred for 30 minutes at 50° C. Formaldehyde (0.02 mM) solution was added at a rate of 0.1 g/min to lignin-triethylene tetramine solutions.

The particle was washed in phosphate buffer (0.5 mM) and stored at 4° C. for bacteriophages immobilization.

B. Immobilization of Bacteriophages on Modified Lignin Nanoparticle

Immobilization of bacteriophages on lignin nanoparticles were performed by overnight incubation of 1 ml of 109 pfu/ml viruses with 5 ml of amine functionalized (10 mg/ml), with gentle shaking at room temperature on an orbital rotator for 3 hours. The unbound bacteriophages were removed by washing the lignin nanoparticle six times with phosphate buffered saline and Tween 20 solution (0.5 mM) (PBST).

Bacteriophages linked to lignin nano particles were collected using centrifugation at 6000 rpm, re-suspended in 1 ml of 0.5 mM PBST buffer, and stored at 4° C. until they were used.

Bacteriophages were enumerated in the initial solution, supernatant/washing solutions, and the number of phages immobilized on magnetic particles was estimated by subtraction.

Example 4: Immobilization of Bacteriophages on Lignin Modified Magnetic Particles A. Synthesis of Lignin Modified Magnetic Particles 10 mmoles of ferric chloride and 0.1 grams of lignin were mixed in 100 ml of water solution. 10 mmol of ferrous chloride was dissolved in 5 ml of water and added dropwise to the solution. The solution was stirred with dropwise addition of 4.5 ml of 30% ammonium hydroxide and stirred at 70° C. for 1 hour. The resulting particles were separated by a magnet. The colloid had a size of ~60-100 nm by light scattering.

To 10 ml of nano particle (10 mg/ml), 0.1 M Tetramethylethylenediamine (TEMED) buffer (pH 5) and 0.2 g of 1-ethyl-3-(dimethylaminopropyl) carbodiimide hydrochloride at room temperature was added followed by 0.5 ml 1,2 ethylene diamine was added. The solution after stirring was centrifuged and washed three times in deionized water.

B. Immobilization of Bacteriophages on Lignin Modified Magnetic Particles

Immobilization of bacteriophages on lignin modified magnetic particles were performed by overnight incubation of 1 ml of $10^9$ pfu/ml viruses with 5 ml of modified magnetic beads (10 mg/ml), with gentle shaking at room temperature on an orbital rotator for 3 hours. The unbound bacteriophages were removed by washing the lignin modified magnetic particles six times with phosphate buffered saline and Tween 20 solution (0.5 mM) (PBST).

Bacteriophages linked to lignin modified magnetic particles were collected using a permanent magnet, re-suspended in 1 ml of 0.5 mM PBST buffer, and stored at 4° C. until they were used.

Bacteriophages were enumerated in the initial solution, supernatant/washing solutions, and the number of phages immobilized on lignin modified magnetic particles was estimated by subtraction.

Example 5: Preparation of Microbicide Corrosion Inhibitor

The corrosion inhibitor was prepared by the following procedure:

1. To a solution of 75 ml of diethylene glycol, 25 ml of diesel was added.
2. The same solution 1 ppm of 1-Butyl-3-methyilimidazolium chloride was added followed by 10 ppm of dimethyl aminopropylamine as stabilizer. The solution was mixed well in an agitator at 220 rpm for 1 hour.
3. Finally, corrosion inhibitor was prepared by adding 0.025 g of lignin modified magnetic particles having bacteriophages concentration of above $10^9$ PFU mL−1 was added and agitated at 300 rpm for 2 hours.

Test run in flask, pH was adjusted, and phage was added externally, after 4 hours count was done. The details of phage release at different pH are shown in below mentioned table 1.

TABLE 1

| Phage release at different pH | |
|---|---|
| pH | Microbial count CFU/ml |
| 8 | $2.8 \times 10^4$ |
| 7 | $2.2 \times 10^5$ |
| 6.5 | Nil |
| 6 | Nil |
| 4 | Nil |

Example 6: MIC Mitigation Study

To test the MIC activity, 500 gm of muck sample was collected and inoculated in a media having the following composition (g/l): $KH_2PO_4$-0.5; $NH_4Cl$-1; $Na_2SO_4$-0.1; $CaCl_2.6H_2O$-1; $MgCl_2.7H_2O$-2, Sodium lactate-3.5; Yeast extract-1; Ascorbic acid-0.2; Thioglycolic acid-0.2 and Ferrous sulphate-0.5 gm. After 72 hours, the total microbial count was noted, and the phage-based biocide as described in step-3 was added. After 24 hours the sample was collected, centrifuged at 10,000 rpm and analyzed for microbial count. Table-2 represents the microbial count before and after the phage-based microbicide addition. As observed from the table-2 below, when the individual components of the phage-based microbicide was used, no significant MIC reduction was observed. However, when the whole composition was added, complete MIC mitigation was observed. This indicates that all the components in the phage-based microbicide work synergistically to effectively reduce MIC.

TABLE 2

Microbial count before and after the phage-based microbicide addition

| | | Microbial count (CFU/g) | | | | | | | |
|---|---|---|---|---|---|---|---|---|---|
| | | Before | After addition of present composition | | | | | | |
| S. No. | Type of bacteria | addition of present composition Control | Magnetic nano-particle (A) | Lignin nano-particle (B) | Bacteriophages (C) | A + C | A + B | B + C | A + B + C |
| 1. | SRB | $6.9 \times 10^7$ | $7.2 \times 10^7$ | $2.2 \times 10^4$ | $2.2 \times 10^2$ | $2.28 \times 10^2$ | $2.9 \times 10^7$ | NIL | NIL |
| 2. | IRB | $7.2 \times 10^8$ | $4.6 \times 10^8$ | $2.2 \times 10^4$ | $8.3 \times 10^2$ | $5.6 \times 10^2$ | $2.0 \times 10^4$ | Nil | Nil |
| 3. | HAB | $4.2 \times 10^{11}$ | $2.3 \times 10^{11}$ | $1.2 \times 10^5$ | $1.4 \times 10^4$ | $1.2 \times 10^4$ | $3.2 \times 10^5$ | Nil | Nil |
| 4. | SLIM | $2.8 \times 10^7$ | $4.8 \times 10^7$ | $5.5 \times 10^4$ | $3.5 \times 10^5$ | $6.2 \times 10^5$ | $2.5 \times 10^4$ | Nil | Nil |
| 5. | APB | $4.5 \times 10^4$ | $6.3 \times 10^4$ | $4.3 \times 10^5$ | $5.3 \times 10^2$ | $4.1 \times 10^2$ | $2.3 \times 10^5$ | Nil | Nil |

MIC inhibition by phage isolated by the present method as compared to one isolated by conventional method is shown in table-3 below:

TABLE 3

MIC inhibition by phage isolated by the present method.

| Conditions for isolation of phage/Test conditions | MIC inhibition by phage (mpy) | Microbial count CFU/ml |
|---|---|---|
| Present method | 0.53 mpy | Nil |
| Conventional method | 4.56 mpy | $2.3 \times 10^4$ |
| Control | 7.4 mpy | $8.9 \times 10^{12}$ |

Example 7: Treatment of MIC

For the treatment of MIC in pipeline, muck sample was obtained at Vadinar, Gujarat, India from Salaya-Mathura Pipeline (SMPL) of Indian Oil Corporation Ltd., India. The phage source used, the water from aeration tank of Panipat refinery wastewater treatment, Haryana, India. The phage was enriched as per details provided in above example. Bacteriophages present in an amount of $10^{10}$ PFU mL$^{-1}$ in 50% ethanol and 50% diesel solution along with Triethylammonium acetate at 1 ppm; and diethanolamine at 8 ppm concentration. Such obtained phage cocktail was used for inhibition of MIC causing microbes in muck sample using standard microbiological tests and their mediated corrosion.

Corrosion protection ability of the phage cocktail was evaluated in presence and absence of muck from pipeline having microbiologically influenced corrosion (MIC) and was evaluated in aggravated static and dynamic laboratory conditions. The mild carbon steel coupon was polished and washed with water and acetone. The diameter and thickness of each coupon was determined. The static test was conducted in beakers while dynamic test was conducted by dynamic 'Wheel test'. The phage cocktail was initially evaluated for their ability to protect from corrosion in static test and further evaluated in dynamic test. The static test was conducted for around 60 days while dynamic test was conducted for 30 days. The experiments were terminated after removing the coupons and washed by neutralized acid to remove the corrosion products, and subsequently rinsed with sterile distilled water, and then dried. Final weight of the coupons in each system was recorded and corrosion rate of the metal coupons were calculated according to following formula:

$$\text{Corrosion rate} = (K \times W)/(A \times T \times D)$$

Where, K=3450000 (constant used to determine corrosion rate in miles per year (mpy)); T=Time of exposure (h); W=Weight loss (g); D=Density (g/cm3); A=Surface area (cm$^3$).

In the wheel test, the coupon as mentioned above was kept in different conditions namely in presence of muck sample alone or in presence of muck and phage cocktail. The results of wheel test after 45 days are shown in table 4 below.

Table-4 Muck sample: count $8.0 \times 10^8$ cfu/g; speed: 12-16 rpm; Temperature: 38-400 C; Phage cocktail: $10^9$ PFU/ml, wherein A*: 125 ml of diesel with 2% water containing 70-ppm chloride in form of HCl and corrosion coupon.

TABLE 4

Corrosion rate (mpy) in Wheel test after 45 days.

| S. No. | Test condition | Corrosion rate (mpy) |
|---|---|---|
| 1 | A* | 6.4 |
| 2 | A* + muck | 8.2 |
| 3 | A* + muck + phage cocktail | 0.7 |

Accordingly, the phage cocktail of present disclosure is effective in corrosion inhibition with corrosion rate: 0.7 mpy thus providing protection from corrosion.

We claim:

1. A method for mitigating or eliminating microbially influenced corrosion (MIC) at a site of interest, the method comprising:
   (i) obtaining a sample from the site of interest and identifying and culturing target bacterial strain;
   (ii) identifying and obtaining bacteriophages against MIC causing microbes from the sample;
   (iii) immobilizing or encapsulating the obtained bacteriophages on a nano-magnetic particle, nano-lignin or a combination thereof;
   (iv) preparing a microbicide corrosion inhibitor composition by adding at least one phage releasing agent and a stabilizer to a combined solution of alcohol and hydrocarbon followed by adding immobilized or encapsulated phages;
   (v) subjecting the site of interest with the microbicide composition to affect a reduction or elimination of microbially influenced corrosion (MIC)
   wherein the culturing of the target bacterial strain in step (i) is performed in the presence of microbial antibiotics in a sub-optimal concentration of $\frac{1}{15}^{th}$ of minimum inhibitory concentration and wherein the bacteriophages are selectively released at a pH in the range of 6.5 to 4 in MIC condition, and wherein the bacteriophages are immobilized on a magnetic nanoparticle using binders having terminal aldehyde or epoxy groups and wherein the binders are selected from the group consisting of glutaraldehyde, and diglycidyl ether.

2. The method as claimed in claim 1, wherein the immobilization of bacteriophages is attained by a process selected among ultrasonication, shaking, covalent or charge directed immobilization process.

3. The method as claimed in claim 1, wherein the nano-magnetic particle or nano lignin is functionalized with an amine or carboxylic functionalizing agent and is having a carbon chain of length between 3 to 12; and wherein the functionalizing agent has exposed primary or secondary amine, amino acids, amine functionalized metal organic frameworks, chitosan, or N-hydroxysuccinimide, 1-ethyl-3-(3-(dimethylamino)propyl) carbodiimide hydrochloride.

4. The method as claimed in claim 1, wherein the alcohol in the microbicide corrosion inhibitor composition is selected from the group consisting of ethanol, isopropanol, glycol, ethylene glycol, diethylene glycol, 1, 2-propylene glycol, dipropylene glycol, tripropylene glycol, glycol ether, butyl glycol, butyl diglycol, a glycol ester, butyl diglycol acetate, 2, 2, 4-trimethylpentanediol monoisobutyrate, polyethylene glycol, polypropylene glycol, benzyl alcohol, n-butyl alcohol, benzyl alcohol, 2,4-dichlorobenzyl alcohol and 2-phenoxyethanol and a combination thereof;
wherein the hydrocarbon in the microbicide corrosion inhibitor composition is selected from the group consisting of diesel, petrol, kerosene, alkenes, cyclohexane and a petroleum refining liquid fuel;
wherein the phage releasing reagent in the microbicide corrosion inhibitor composition is a protic and aprotic ionic liquid and is selected from the group consisting of 1-Benzyl-3-methylimidazolium tetrafluoroborate ([BzMIM] [BF4]), 1-Butyl-3-methyilimidazolium chloride ([BMIM] [Cl]), Triethylammonium acetate (TEAA), Choline dihydrogen phosphate ([Chol] [DHP]), Choline serinate ([Chol] [Ser]), Ethylammonium nitrate (EAN), Tetrabutylphosphonium bromide (TBPBr) and a combination thereof; and
wherein the stabilizer in the microbicide corrosion inhibitor composition is selected from the group consisting of N,N-dimethylethanolamines, such as (N,N-dimethyl-aminoethoxy) ethanol; dimethylethanolamine; triethanolamine; methyl diethanol amine; ethanolamine; diethanolamine; other cyclic amines including morpholine, methyl morpholine, ethylmorpholine, piperidine, alkylpiperidines, piperazine, alkylpiperazines; ethylene amines including DETA, TETA, TEPA, and the like; alkyl amines including methyl amine, dimethyl amine, alkyl methylamines, dimethyl alkylamines; methyl amino propylamine; dimethyl aminopropylamine; dimethyl aminoethylamine; methyl aminoethylamine and a combination thereof.

5. The method as claimed in claim 1, wherein the step (v) of subjecting the site with the microbicide corrosion inhibitor composition is preceded by repetitive chain of pigging with the help of cleaning brush pig.

6. The method as claimed in claim 1, wherein the target bacterial strain is an anaerobic bacterium causing corrosion by depositing a bacterial biofilm on a metal surface and wherein the target bacterial strain is selected from the group consisting of sulfate-reducing bacteria (SRB), iron-oxidizing/reducing bacteria (IRB), bacteria secreting organic acids (APB), exopolymers or slime (SPB), methanogen, nitrate reducing bacteria and low nutrient bacteria and a combination thereof.

7. The method as claimed in claim 1, wherein the site of interest is a metal surface of an equipment for refining, storing, transporting of oil and natural gas.

8. The method as claimed in claim 1, wherein the sample is a muck sample obtained from Municipal solid waste (MSW), Sewage treatment plant (STP) or industrial wastewater samples by pigging.

9. The method as claimed in claim 1, wherein the microbicide corrosion inhibitor composition comprises bacteriophages in an amount of at least $10^9$ PFU mL$^{-1}$; at least one alcohol in amount of 50-75% (vol/vol); a hydrocarbon in an amount of 25-50% (vol/vol); at least one phage releasing agent in an amount of 1-5 ppm; and a stabilizer in an amount of 6-10 ppm is effective for reducing or eliminating microbially influenced corrosion (MIC) at the site of interest.

10. A microbicide composition for mitigating or eliminating microbiologically influenced corrosion (MIC) at a site of interest, said composition comprising:
(i) bacteriophages in an amount of at least $10^9$ PFU mL$^{-1}$;
(ii) at least one alcohol in amount of 50-75% (vol/vol);
(iii) a hydrocarbon in an amount of 25-50% (vol/vol);
(iv) at least one phage releasing agent in an amount of 1-5 ppm; and
(v) a stabilizer in an amount of 6-10 ppm.

* * * * *